United States Patent [19]

Johnsson et al.

[11] Patent Number: 4,533,516

[45] Date of Patent: Aug. 6, 1985

[54] APPARATUS FOR THE TRANSFER OF ONE OR MORE SUBSTANCES BETWEEN A GAS AND A LIQUID

[75] Inventors: Bo A. Johnson, Landskrona; Ingvar E. Losell; Sune H. Palmqvist, Kaj O. Stenberg, all of Staffanstorp, all of Sweden

[73] Assignee: Gambro Cardio AB, Sweden

[21] Appl. No.: 395,283

[22] Filed: Jul. 6, 1982

[30] Foreign Application Priority Data

Jul. 7, 1981 [SE] Sweden ............................ 8104219

[51] Int. Cl.³ .............................................. A61M 1/03
[52] U.S. Cl. .................................... 422/46; 422/45; 422/47; 261/DIG. 28
[58] Field of Search ................................ 422/46, 47; 261/DIG. 28; 128/DIG. 3; 55/255, 256; 210/177

[56] References Cited

U.S. PATENT DOCUMENTS

| 4,138,464 | 2/1979 | Lewin | 422/46 |
| 4,140,635 | 2/1979 | Esmond | 422/46 X |
| 4,158,693 | 6/1979 | Reed et al. | 422/46 |
| 4,180,896 | 1/1980 | Reed et al. | 422/46 X |
| 4,261,951 | 4/1981 | Milev | 422/46 |
| 4,374,088 | 2/1983 | Steinberg et al. | 422/46 |

FOREIGN PATENT DOCUMENTS 0035266 9/1981 European Pat. Off. .

Primary Examiner—Michael S. Marcus

Attorney, Agent, or Firm—Lerner, David, Littenberg, Krumholz & Mentlik

[57] ABSTRACT

An apparatus for the transfer of one or more substances between a gas and a liquid, for example between an oxygen-containing gas and blood, is disclosed. The apparatus includes a plurality of concentric vessels which define a flow path for the liquid, and which includes along a portion of the path an annular heat exchange chamber having a first end at which the liquid is introduced into the chamber and a second end at which the liquid is conducted from the chamber. A heat exchanger is supported in the heat exchange chamber for conducting a heat exchange fluid in heat exchange relationship with the liquid as the liquid flows through the chamber. Gas in the form of bubbles is introduced into the liquid as the liquid is conducted along the flow path to thereby effect transfer of substances between the gas and the liquid, the gas being introduced upstream of the first end of the heat exchange chamber. A plurality of throttling ports are arranged about the periphery of the annular heat exchange chamber at the second end of the chamber for conducting the liquid from the heat exchange chamber. Downstream of the second end of the heat exchange chamber, excess gas is removed from the liquid together with substances transferred from the liquid to the gas. By means of this arrangement, a very uniform and homogeneous flow around the entire periphery of the heat exchange chamber is provided, which in turn insures that a good heat transfer and gas exchange is obtained.

14 Claims, 7 Drawing Figures

APPARATUS FOR THE TRANSFER OF ONE OR MORE SUBSTANCES BETWEEN A GAS AND A LIQUID

FIELD OF THE INVENTION

The present invention relates to apparatus for the transfer of one or more substances between a gas and a liquid, the gas being introduced into the liquid in the form of bubbles from which substances are transferred to the liquid, and whereupon excess gas is removed together with any substances transferred from the liquid to the gas.

The apparatus in accordance with the present invention is mainly intended to be used for the oxygenation of blood, that is to say as an oxygenator. It is clear, however, to those versed in the art that the construction in accordance with the present invention can also be used for many other purposes. For example, the invention may also be used substantially wherever substances from a gas are to be made to react with or to dissolve in a liquid, as well as whenever substances are to be exchanged between gases and liquids.

BACKGROUND OF THE INVENTION

Insofar as oxygenators are concerned, three main types are generally known. The oldest is probably the type where a blood film is formed in direct contact with an atmosphere containing oxygen. In the second type, the oxygen is made instead to diffuse through a semipermeable membrane from an atmosphere containing oxygen on one side of the membrane to the blood on the other side. The third type, to which the apparatus in accordance with the present invention belongs, is generally known as bubble oxygenator. In this type, gas bubbles containing oxygen are introduced directly into the blood so as to directly act on the same. After the desired action, the excess gas is removed from the blood together with any substances transferred from the blood to the gas.

Examples of constructions of bubble oxygenators are shown, for example, in U.S. Pat. Nos. 3,175,555; 2,934,066; 3,545,937; 4,037,622; 3,468,831; 3,488,158; 3,615,238; 4,058,369; 3,578,411; 3,291,568; 4,033,724; 3,827,860; 3,853,479; 4,067,696; 4,065,254; 4,138,464; 4,138,288.

More particularly, the present invention is an improvement of the apparatus shown and described in international patent application No. PCT/SE80/00096, filed Apr. 3, 1980 and published under No. WO 81/02836 Oct. 15, 1981.

SUMMARY OF THE INVENTION

In accordance with the present invention, there is provided an apparatus for the transfer of one or more substances between a gas and a liquid in which the apparatus comprises liquid conduction means defining a flow path for a liquid and which includes along a portion of the flow path means defining an annular heat exchange chamber having a first end at which the liquid is introduced into the heat exchange chamber and a second end at which the liquid is conducted from the heat exchange chamber, and heat exchange means supported in the heat exchange chamber for conducting a heat exchange fluid in heat exchange relationship with the liquid as the liquid flows through the heat exchange chamber. Gas introduction means are provided for introducing a gas in the form of bubbles into the liquid as the liquid is conducted along the flow path to thereby effect transfer of substances between the gas and the liquid, the gas introduction means being located upstream of the first end of the heat exchange chamber. Also, a plurality of throttling ports are arranged about the periphery of the annular heat exchange chamber at the second end of the heat exchange chamber for conducting the liquid from the heat exchange chamber, and removal means are provided along the flow path downstream of the second end of the heat exchange chamber for removing excess gas from the liquid together with any substances transferred from the liquid to the gas. By means of this arrangement, a very uniform and homogeneous flow around the entire periphery of the heat exchange chamber is provided. This in turn insures that a good heat transfer and gas exchange is obtained.

In accordance with a preferred embodiment, the throttling ports each include smooth entrance and exit portions in order to prevent any damage to the liquid in connection with the throttling action which is achieved as the liquid is conducted through the throttling ports. This is most important when the apparatus in accordance with the present invention is utilized as a blood oxygenator since it is most desirable to prevent damage to the blood. The smooth entrance and exit portions for the throttling ports may comprise smooth doubled curved shapes for the ports, one curved portion being provided at the entrance of the port and one curved portion being provided at the exit of the port.

Still further in accordance with a preferred embodiment, the annular heat exchange chamber is comprised of an inner wall and an outer wall, and the throttling ports are defined in one of the inner and outer walls at the second end of the heat exchange chamber. More preferably, the annular heat exchange chamber is formed between an inner inlet conduit and a outer vessel arranged concentrically with respect to the inlet conduit, the vessel being open at its upper end. In such a construction, the throttling ports may comprise recesses in the top edge of the vessel, and a cover member may be provided in tight contact against the portions of the top edge of the vessel which are not occupied by the recesses. The inlet conduit may advantageously serve as the means for introducing the gas and blood into the apparatus.

Still further in accordance with a preferred embodiment, the apparatus includes an outer casing arranged outside of the vessel and which includes means defining an annular skimming chamber between the vessel and the outer casing. Also, the removal means may comprise filter means arranged intermediate the vessel and the casing and in communication with the skimming chamber in order to facilitate final breaking down and removal of the gas bubbles in the liquid. Preferably, the filter means is arranged obliquely with respect to the vessel to provide a wedge shaped collecting space for the liquid in which the collecting space is wider toward the upper end of the vessel and narrower toward the lower end of the vessel so that the throttling ports communicate initially with the wider portion of the collecting space. This construction has proven advantageous from the viewpoint of assembly of the various components of the apparatus as well as from the viewpoint of efficiency.

Also in accordance with a preferred embodiment, the heat exchange means is suitably made shorter in length than the heat exchange chamber, and is supported in the chamber so as to be separated from the lower end of the chamber in order to provide a mixing chamber. In this manner, the mixing of the gas bubbles into the liquid is enhanced irrespective of the design of the heat exchange means. Also, preferably the gas introduction means comprises a plurality of holes of a well defined size evenly distributed in a circular array adjacent the lower end of the heat exchange chamber. This is advantageous for the formation of relatively larger size bubbles which are partly broken down and/or transformed into the liquid during passage of the liquid through the heat exchange chamber, and which are then further broken down during passage through the throttling ports. In this regard, it is to be noted that when the apparatus is used as a blood oxygenator, the transfer of carbon dioxide is normally considered to be improved by large bubbles, while the transfer of oxygen is considered to be more effective by means of smaller sized bubbles.

These and further features and characteristics of the present invention will be apparent from the following detailed description in which reference is made to the enclosed drawings which illustrate preferred embodiments of the present invention.

DESCRIPTION OF THE PREFERRED EMBODIMENTS

The apparatus of the present invention is mainly intended for use as an oxygenator in which the liquid comprises blood, and the gas comprises oxygen or an oxygen containing gas from which oxygen is to be transferred to the blood and to which carbon dioxide is to be transferred from the blood. Accordingly, the present invention will be described with reference to such a use. However, it is to be appreciated that the present invention can also be used for other purposes, for example substantially wherever substances from a gas are to be made to react with or to dissolve in a liquid as well as wherever substances are to be exchanged between gases and liquids.

Figure 1:
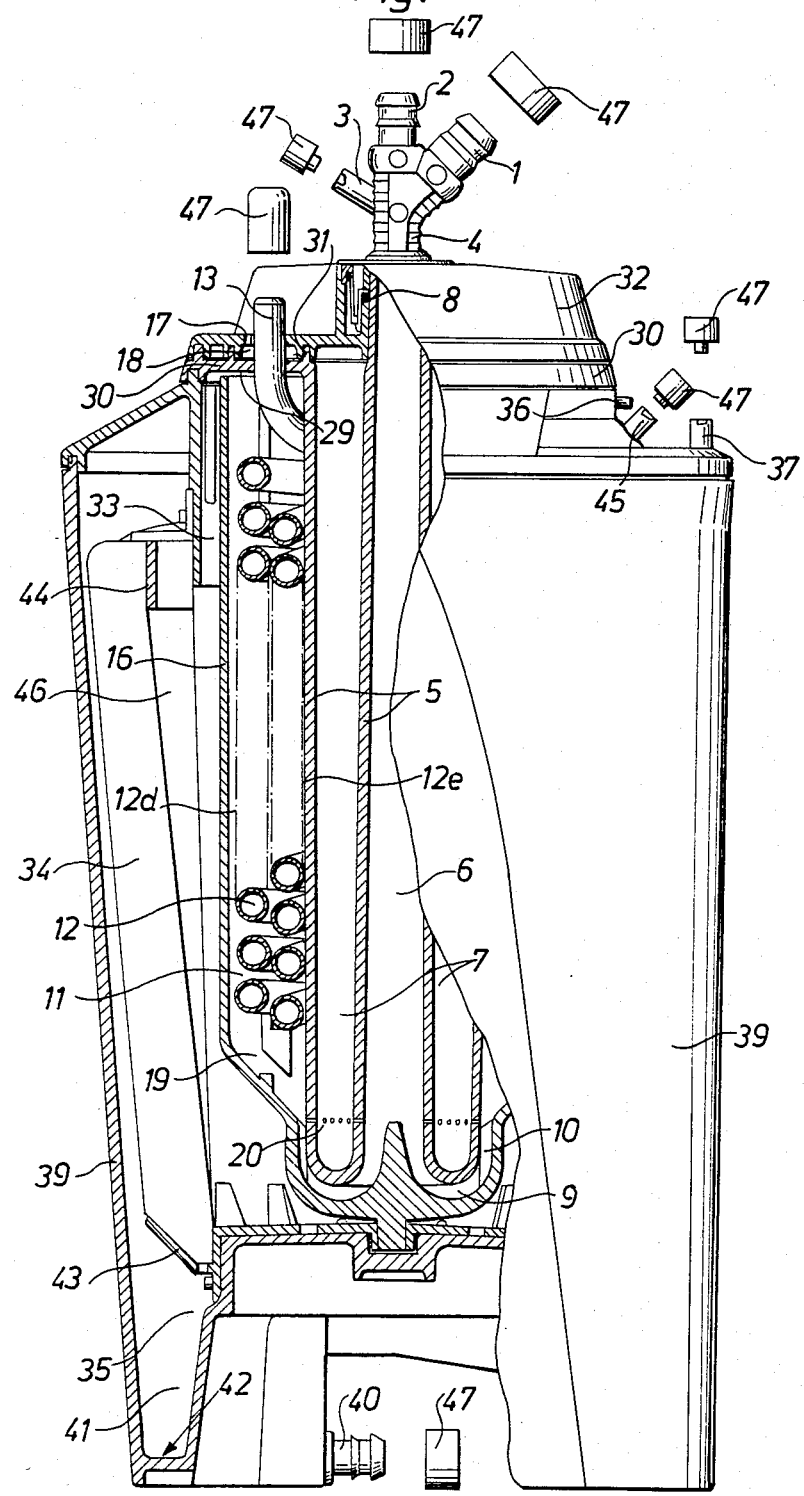
FIG. 1 is a longitudinal sectional view of an apparatus in accordance with the present invention, the particular embodiment shown being that of an oxygenator for the transfer of one or more substances between blood and an oxygen-containing gas.

Referring now to the drawings wherein like reference characters represent like elements, there is shown in FIG. 1 an oxygenator for oxygenating, for example, venous blood supplied from a patient. The blood is introduced into the apparatus via an inlet nozzle 1 arranged at the top of the apparatus. The nozzle 1, together with a second inlet nozzle 2 and a sampling nozzle 3, is arranged on a branch pipe 4 which is freely rotatable with respect to the remaining parts of the oxygenator. The branch pipe 4 is threaded onto a double-walled inlet pipe or conduit 5 arranged centrally in the oxygenator. The conduit or pipe 5 contains an inner central liquid inlet duct 6 and an outer annular gap 7 for the supply of a gas. Between the inlet pipe 5 and the branch pipe 4 a packing 8 is provided. Thus the blood is caused to flow vertically downwardly through the duct 6 and, via a smooth passageway 9, out into a narrow annular gap 10. The passageway 9 thus serves to smoothly guide and turn the flow upwardly. From the gap 10, the fluid subsequently passes into a widened annular vertical cylinder space or chamber 11 which is defined between the pipe or conduit 5 and an intermediate, concentrically arranged vessel 16. The chamber 11 contains a het exchanger 12 and thus forms a heat exchange chamber in which the blood is heated and the mixing of the gas into the blood is enhanced.

Figure 2:
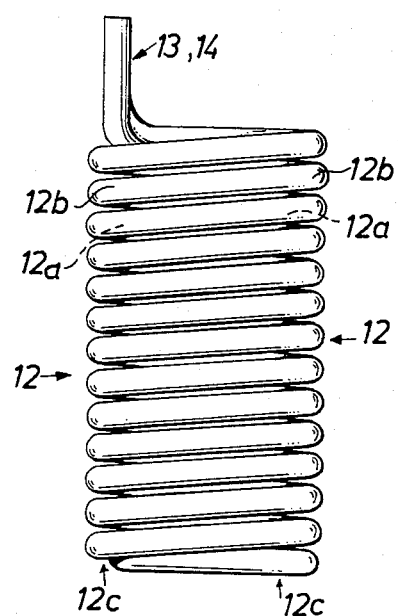
FIGS. 2 and 3 illustrate a side view and an end view respectively of a heat exchange forming part of the oxygenator shown in FIG. 1.
Figure 3:
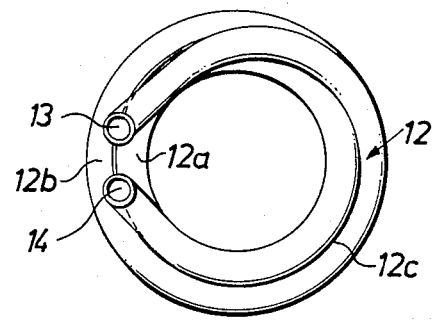

The heat exchanger 12, which is more clearly shown in FIGS. 2 and 3, is provided with a fluid inlet 13 and a fluid outlet 14. The heat exchanger 12 preferably comprises a single pipe which consists of two separate parts or sections, namely an inner section 12a and an outer section 12b respectively. Both of these sections 12a and 12b are coiled in a helical form, for example in a left-hand twist and right-hand twist, respectively. The two sections 12a, 12b, are radially spaced from one another to provide a gap 12c through which the blood may flow upwardly in heat exchange relationship with the heat exchange fluid being conducted through the heat exchanger 12. Between the heat exchanger 12 and the outer and inner walls respectively of the annular chamber or space 11, the heat exchanger 12 forms further gaps 12d and 12e, respectively.

Such an arrangement provides a very compact construction of high efficiency with regard to heat transfer as well as with regard to gas exchange as the liquid-gas mixture is introduced through the chamber 11. For instance, the heat exchanger 12 can be dimensioned and constructed to withstand the highest possible pressure to which it may conceivably be subjected. Also, the risk of leakage between the heat transfer fluid and the liquid-gas mixture can be minimized. Still further, high safety from the point of view of leakage is achieved by virtue of the two sections 12a, 12b being coiled in a helical manner from one and the same pipe or conduit. Also, by using a left hand twist for one pipe section 12a and a right hand twist for the other pipe section 12b, the inlet and outlet for the heat transfer fluid may conveniently be arranged at the same end of the heat exchanger 12. This construction also facilitates the assembly of the heat exchanger within the heat exchanger chamber 11 since the heat exchange 12 can simply be inserted through the open end of the vessel 16 which defines, with the pipe or conduit 5, the heat exchange chamber 11. In particular, the annular gap 10 and the annular heat exchange chamber 11 formed above it are designed to be located between the centrally arranged gas and liquid inlet pipe or conduit 5 and an intermediate vessel 16 which is open at the top.

The gas, which consists of oxygen or an oxygen mixture when the device is used as an oxygenator, is supplied via an opening 17 into an inlet chamber 18, and from there, via a sterile filter (not shown) and further ducts, into the annular space 7 in the inlet conduit 5. A series of holes 20 for introducing gas in the form of bubbles into the blood are evemly distributed along the periphery of the gap 10 at the upper end of the latter.

Thus, the gas will be pressed out and introduced into the blood at the elevation where the gap 10 passes over into the widened annular space or chamber 11. Through this arrangement, a very efficient mixture of blood and gas is achieved. The mixture of gas and fluid thus flows vertically upwards through the gaps 12c, 12d, and 12e.

Preferably, the heat exchanger 12 is supported in the chamber 11 so that the lower end of the heat exchanger 12 is spaced above the lower end of the chamber 11 to thus define a mixing chamber 19 in which bubble formation is enhanced. The mixing chamber 19 thus serves to improve the mixing of the gas bubbles into the blood. The mixture process is further improved by means of the gaps 12c, 12d, and 12e provided between the fluid conduit sections 12a and 12b and between the sections 12a and 12b and the inner and iouter walls forming the annular heat exchanger chamber 11. In particular, the provision of the gaps 12c, 12d and 12e serves to improve gas exchange by breaking down of the gas bubbles into a smaller size, which may be more easily transferred into the blood. Here it is to be noted that the transfer of carbon dioxide is normally considered to be improved by large size bubbles while the transfer of oxygen is considered to be more effective by means of small size bubbles. Also, the gaps 12c, 12d and 12e serve to enhance the heat transfer between the heat exchange fluid and the blood as it is conducted upwardly through the heat exchange chamber 12. Still further, the construction is completely free of leakage problems and is very suitable from the point of view of installation.

In the upper end of the heat exchange chamber 11, a throttling passageway 29 is provided. In the embodiment shown in FIG. 1, the throttling passageway 29 comprises an annular throttling gap 29 which is shown schematically in FIG. 1 in the form of a spillway between the top edge of the vessel 16 and a lid 30 provided above the same. This lid is designed so as to be integral with the double-walled inlet pipe or conduit 5 and is connected in turn via seals 31 to an outer lid 32 comprising, among other things, the gas inlet chamber 18 and the sterile filter (not shown).

In accordance with the present invention, the gap 29 preferably is replaced by throttling ports 29a, which are shown more clearly in the embodiment shown in FIGS. 4–7 and which will be described in more detail in connection with these Figures. The throttling ports 29a serve to insure that a uniform and homogeneous flow is provided around the whole periphery of the heat exchange chamber 11. In this manner, both a good heat transfer and gas exchange is achieved.

From the spillway 29 or the throttling ports 29a the gas-blood mixture flows downwardly through an annular gap or chamber gap 33 between the intermediate vessel 16 and a filter 34. The blood flows out through the filter 34 into a blood collecting space 35, whilst the excess gas flows out instead through a gas outlet 36.

The sampling nozzle 3 is intended for the sampling of venous blood. Via the sampling nozzle 37 and a conduit or pipe (not shown), it is possible instead to take samples of arterial blood owing to the fact that this pipe terminates downwardly in the blood collecting space 35.

The intermediate vessel 16 with the inlet conduit 5 arranged therein and the filter 34 arranged outside the same, are enclosed in an outer casing 39 comprising a bottom outlet 40 for the separated fluid or blood phase. The lower part of the bottom of this outer casing 39 is designed as an annular gap 41 with a base 42 sloping evenly towards the bottom outlet 40.

It will thus be noted that the construction of the oxygenator as a whole is comprised of a number of concentric vessels inserted into each other. This construction is advantageous from the viewpoint of sealing the oxygenator after assembly and during use. The outer-most of these is the outer casing 39. Into this is inserted a "vessel" formed of the filter 34 which is limited at the bottom by a base ring 43 and at the top by a fixing ring 44. With the help of the ring 44, the filter 34 is fixed to the outside of the vessel 16 described above as the intermediate vessel. Into the latter is then inserted the inlet pipe or conduit 5 designed as a double-walled vessel.

The base ring 43 and the fixing ring 44 are designed so that the filter 34 is arranged obliquely with respect to the outer wall of the vessel 16 and at the lower end of the annular gap or chamber 33. Through this arrangement, a concial or wedge-shaped collecting space 46 is formed for the collection of the gas and liquid mixture before the same is passed through the filter 34. In this way the blood initially is made to pass through the lower part of the filter 34 and to make use only at higher flow rates also of the upper parts of the filter 34. The annular chamber 33 and collecting space 46 thus constitutes a skimming chamber which, with the filter 34, serves to facilitate the final breaking down and removal of the gas bubbles from the blood. The wedge-shaped collecting space 46 also is advantageous from the viewpoint of assembly of the apparatus.

Numeral 45 designates an inlet nozzle intended for the support of medicine, heparin or other additions to the mixture of gas and blood before the same passes through the filter 34.

With regard to the gas introduction holes 20, in a preferred embodiment there are approximately one hundred holes 20 evenly distributed about the periphery of the gap 10. Each of the holes 20 has an accurately defined diameter. This can be made to be practically exactly 250 $\mu$, for example, with the help of a laser technique. With a length of the holes 20 of approximately 3 mm, it was found that air or other oxygen containing gas will flow through all the holes 20, even at a gas flow as low as 0.75 liter per minute. Also, in the preferred embodiment the gap 10 is approximately 3 mm, which thus provides a good mixture at a standard blood flow of between 2 and 6 liter per minute. However, the device may also be used at higher as well as at lower flow rates. Finally, numeral 47 designates a number of caps for the closing of different openings of the oxygenator.

Figure 4:
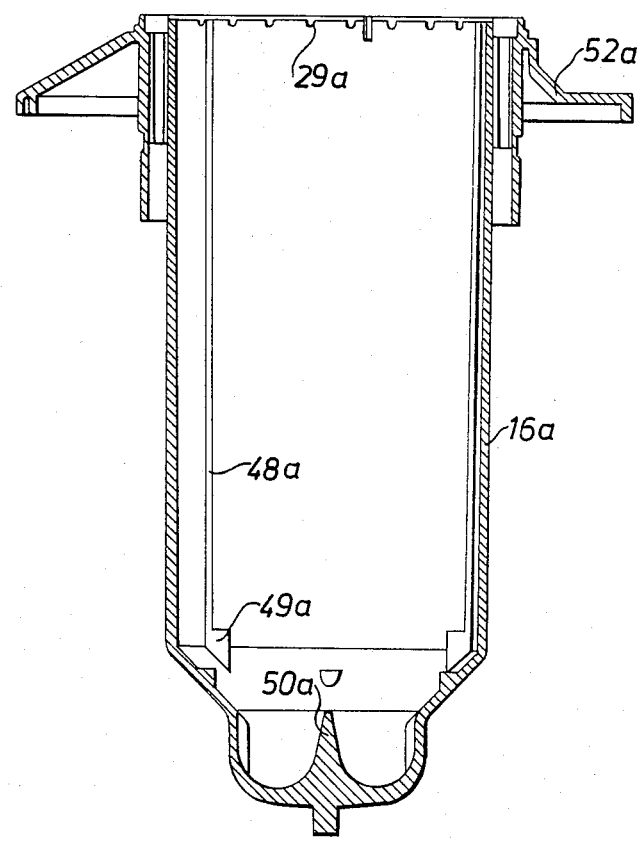
FIG. 4 is a longitudinal section through an intermediate vessel forming part of a modified design for the apparatus of the present invention.
Figure 5:
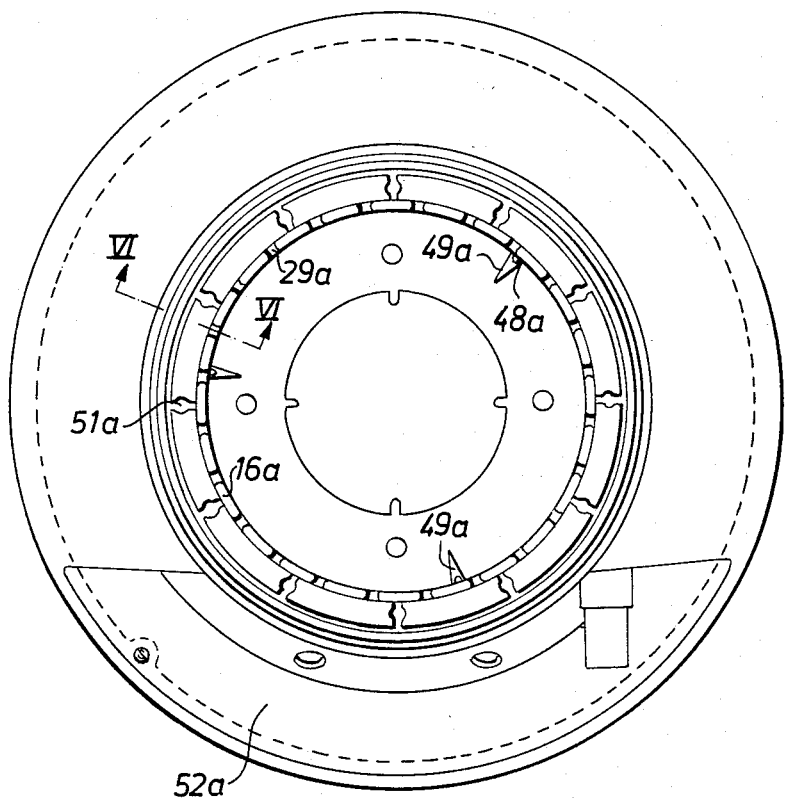
FIG. 5 is an end view of the vessel shown in FIG. 4, as seen from the open upper end of same.
Figure 6:
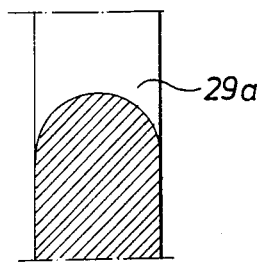
FIG. 6 illustrates a sectional view, taken along the line VI—VI of FIG. 5, of a throttling port provided in the top edge of the vessel shown in FIGS. 4 and 5.
Figure 7:
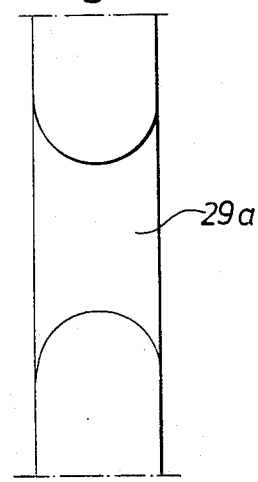
FIG. 7 is a sectional view of the throttling port shown in FIG. 6, taken along lines VII-VII of FIG. 6.

The vessel shown in FIGS. 4 and 5 corresponds in principle to the vessel 16 in FIG. 1, but has been somewhat modified to illustrate another form of the apparatus of the present invention. Accordingly, the same reference designations have been used, but with the addition of a small letter a. The vessel is thus designated 16a and the throttling ports, which replace the gap or spillway 29, are designated 29a. As best seen in FIGS. 4 and 5, the throttling parts 29a comprise recesses which are evenly distributed about the periphery of the annular heat exchange chamber 11 in the upper edge of the wall of the intermediate vessel 16a. Thus, the lid or cover 30 will be placed in tight contact with the portions of the upper edge of the vessel 16a between the recesses defining the ports 29a. The even distribution of ports 29a about the periphery of the heat exchange chamber serves to insure a uniform flow, and thus to enhance heat transfer and gas exchange. Further, the ports 29a are each provided with a smooth entrance and exit portion which may be of a double-curved shape or configuration, as as best seen in FIGS. 6 and 7. This shape is very important, as it ensures that the blood is handled gently in spite of the blood being subjected to a throttling action through these ports 29a.

Numeral 48a designates three ribs which together define the size of the gap corresponding to the gap 12d formed between the heat exchanger 12 and the vessel 16a. Three shoulders 49a define the lower limit or position of the heat exchanger 12, and thus the upper limit of the mixing chamber corresponding to the chamber 19 in FIG. 1. Numeral 50a designates a point which serves to ensure that the blood is deflected smoothly from a flow directly vertically downwards to one directed upwards. Further, the intermediate stage 51a is provided with thickened portions so as to facilitate the outflow of the plastic when the vessel 16a and the lid 52a attached are manufactured by injection moulding.

While the preferred embodiments of the present invention have been shown and described, it will be understood that such are merely illustrative and that changes may be made without departing from the scope of the invention as claimed.

What is claimed is:

1. Apparatus for the transfer of one or more substances between a gas and a liquid, said apparatus comprising:
    a heat exchange chamber, said heat exchange chamber defining a flow path from a first end thereof to a second end at which liquid is conducted therefrom, heat exchange means supported in said heat exchange chamber for conducting a heat exchange fluid in heat exchange relationship with said liquid as said liquid flows through said heat exchange chamber;
    gas introduction means for introducing a gas in the form of bubbles into said liquid as said liquid is conducted along said flow path to thereby effect transfer of substances between said gas and said liquid, said gas introduction means being located upstream of said second end of said heat exchange chamber;
    a cover having an inner surface disposed adjacent said second end of said heat exchange chamber, said second end of said heat exchange chamber being defined by a peripheral edge portion of a wall, and recesses in said peripheral edge portion of said wall cooperating with said inner surface of said cover to provide a plurality of throttling ports for conducting liquid from said heat exchange chamber, said recesses being arranged about the periphery of said heat exchange chamber; and
    removal means alons said flow path downstream of second end of said heat exchange chamber for removing excess gas from said liquid together with any substances transferred from said liquid to said gas.

2. The apparatus of claim 1 wherein said recesses have smooth edges to provide smooth entrance and exit portions to and from said throttling ports.

3. The apparatus of claim 1 wherein said liquid comprises blood, and wherein said gas comprises an oxygen containing gas.

4. The apparatus according to claim 1, wherein said cover is in contact with the portions of said peripheral edge portion of said wall which are not occupied by said recesses.

5. The apparatus according to claim 1, wherein said recesses are substantially uniformly spaced about the periphery of said heat exchange chamber.

6. The apparatus of claim 1 wherein the longitudinal length between said first and second ends of said heat exchange chamber is greater than the longitudinal length of said heat exchange means, and wherein said heat exchange means is supported in said heat exchange chamber to define a mixing chamber between said first end of said heat exchange chamber and said heat exchange means for mixing said gas bubbles into said liquid.

7. The apparatus of claim 6 wherein said heat exchange chamber is oriented vertically with said first end being below said second end; and wherein said gas introduction means comprising a plurality of holes arranged in a circular pattern for the introduction of said gas in the form of bubbles into said liquid adjacent said first end of said heat exchange chamber.

8. The apparatus according to claim 1, wherein said heat exchange chamber is annularly-shaped and said wall defines the outer wall of said annularly-shaped heat exchange chamber.

9. The apparatus of claim 8 wherein said outer wall of said annularly-shaped heat exchange chamber comprises the wall of a vessel, and wherein said annularly-shaped heat exchange chamber has an inner wall which comprises a wall of an inlet conduit concentrically disposed within said vessel.

10. The apparatus of claim 9 further including an outer casing arranged concentrically outside of said vessel and including means defining an annular skimming chamber between said vessel and said outer casing through which said liquid is conducted from said heat exchange chamber; and wherein said removal means comprises filter means arranged intermediate said vessel and said casing and in communication with said skimming chamber.

11. The apparatus of claim 10 wherein said filter means is obliquely oriented with respect to said vessel to provide a wedge shaped collecting space between said vessel and said filter means in which said collecting space is wider toward said second end of said vessel and narrows towards said first end of said vessel so that said throttling ports communicate initially with said wider portion of said collecting space.

12. The apparatus of claim 8 wherein said annularly-shaped heat exchange chamber has an inner wall, and wherein said heat exchange means comprises fluid conduit means having a first fluid conduit section and a second fluid conduit section each arranged in a helical manner in said annularly-shaped heat exchange chamber, said first and second fluid conduit sections being spaced from one another to define a first annular gap along which said liquid may flow in heat exchange relationship with said heat exchange fluid, and said first fluid conduit section being radially spaced from said inner wall of said heat exchange chamber and said second fluid conduit section being radially spaced from said outer wall of said heat exchange chamber to define respectively second and third annular gaps along which said liquid may flow in heat exchange relationship with said heat exchange fluid.

13. The apparatus of claim 12 wherein said fluid conduit sections each include a first end and a second end, and wherein said second ends are coupled to one another to conduct said heat exchange fluid between said first and second fluid conduit sections.

14. The apparatus of claim 13 wherein said first ends of said first and second fluid conduit sections are at the same elevation, wherein one of said fluid conduit sections is coiled in a left hand twist and the other of said fluid conduit sections is coiled in a right hand twist, and wherein said heat exchange fluid is introduced into said first end of one of said fluid conduit sections and is withdrawn from said first end of the other of said fluid conduit sections.

* * * * *